United States Patent [19]

Juarez-Salinas et al.

[11] Patent Number: 4,704,366

[45] Date of Patent: Nov. 3, 1987

[54] PROCESS FOR BINDING IGG TO PROTEIN A

[75] Inventors: Hector Juarez-Salinas, Larkspur; Gary S. Ott, Livermore, both of Calif.

[73] Assignee: Bio-Rad Laboratories, Inc., Richmond, Calif.

[21] Appl. No.: 623,797

[22] Filed: Jun. 22, 1984

[51] Int. Cl.$^4$ .............. G01N 33/566; G01N 33/577; G01N 33/544; G07K 3/12

[52] U.S. Cl. .................................. 436/501; 435/7; 436/529; 436/530; 436/532; 436/548; 436/828; 530/387; 530/402; 530/413; 530/825; 935/108

[58] Field of Search ............... 436/501, 529, 530, 532, 436/548, 828; 530/387, 402, 413, 825; 935/108; 435/7

[56] References Cited

U.S. PATENT DOCUMENTS 4,430,318  2/1984  Langone .......................... 436/501

FOREIGN PATENT DOCUMENTS 0016552 10/1980 European Pat. Off. ............... 435/7
0079221  5/1983 European Pat. Off. ............. 424/85

OTHER PUBLICATIONS

Lindmark et al., J. Immunol. Meth., 62 (1983) 1-13.
Hurrell, ed., Monoclonal Hybridoma Antibodies; Techniques and Applications, CRC Press, Inc., Boca Raton, Fla., 1982, pp. 51-52.
Lehninger, Biochemistry, Worth Publishers, Inc., N.Y., 1970, pp. 133-134.

Primary Examiner—Christine M. Nucker
Attorney, Agent, or Firm—Townsend & Townsend

[57] ABSTRACT

Unusually strong binding of IgG to protein A is achieved by contacting these components in the presence of a medium containing a high concentration of salt. Although such binding is of general utility, a particularly useful application is the purification of monoclonal antibodies from ascites fluid by affinity chromatography.

16 Claims, No Drawings

PROCESS FOR BINDING IGG TO PROTEIN A

BACKGROUND OF THE INVENTION

1. Field of the Invention

This invention relates to the immobilization of immunoglobulins, and particularly the immobilization of IgG's by binding to protein A. Such binding presents a range of utility in immunological techniques, both analytical and preparatory, and is of particular interest in the purification of antibodies, notably monoclonal, from an ascites fluid.

2. Description of the Prior Art

The ability of protein A to bind to the Fc portion of IgG molecules is widely used as a basis for separation of IgG's from other proteins by affinity chromatography. In such separations, protein A is generally immobilized by cross-linking to a solid phase support such as agarose, and the sample is applied as a solution in a buffer which disfavors the binding of other proteins in the mixture. The immunoglobulins are then recovered from the solid phase by elution using buffers of altered composition. The separation achieved, however, is less than complete.

An early disclosure of the binding of certain antibodies to protein A is found in Kronvall et al., *Journal of Immunology*, 105(5): 1116 (1970). An attempt to improve the separation was made by Mackenzie, et al., *Journal of Immunology*, 120(5): 1493 (1978), in which a continuously increasing NaSCN gradient at low pH was used as an elution buffer with a protein A-Sepharose 4B column. Binding was low for $IgG_1$ and $IgG_2$ and reproducibility has been found to be lacking.

An elution sequence characterized by a stepwise decrease in pH at constant low salt concentration was used by Ey et al., *Immunology*, 15: 429 (1978). A substantial amount of $IgG_1$ was found to have bled over into the subsequent fraction, and reproducibility was lacking here also.

Chalon et al., in *Scand. Journal of Immunology*, 9: 359 (1979), achieved partial success in separating various IgG's from IgA and IgM, by dissolving the mixtures in phosphate-buffered saline at pH 7.3, then introducing the solution into a column containing protein A-Sepharose 4B equilibrated to the same buffer. Two peaks emerged with no change in buffer, the second of which to elute containing mostly $IgG_1$. The yields varied from 31% to 73%.

Finally, sixteen different eluents for protein A-Sepharose 4B purification of various IgG's were studied by Bywater et al., *Journal of Immunological Methods*, 64: 1 (1983). No improvement in either separation or yield over previous methods was observed in any of the samples tested.

SUMMARY OF THE INVENTION

It has now been discovered that the binding affinity of protein A for IgG's in general is substantially increased in the presence of a salt concentration of 0.5 moles per liter or higher. The effect is achievable by either equilibrating the protein A with a salt solution of the selected concentration, dissolving the immunoglobulin mixture in such a solution, or both. The unusually strong binding which results is particularly useful in separating these immunoglobulins from other proteins, such as those normally present in an ascites fluid.

DESCRIPTION OF THE PREFERRED EMBODIMENTS

The present invention is applicable to IgG's in general, regardless of source. Preferred IgG's for the purposes of this invention are mouse $IgG_1$, $IgG_{2a}$ and $IgG_{2b}$. The proteins from which the species of interest may be separated are other immunoglobulins, such as, for example, IgM and IgE, and other proteins such as, for example, albumins. The binding affinity of these proteins for protein A is known to be much less than that of IgG's.

Any inorganic salt which is soluble in an aqueous medium may be used. Examples include alkali and alkaline earth metal halides and sulfates. Positively charged ions such as ammonium may be substituted for the metallic ions. The salt must also be nonreactive toward the immunoglobulins, the protein A or any support to which the protein A is bound. The salt concentration may range from about 0.5 M up to the solubility limit, preferably from about 1.0 M to about 4.0 M. The exact pH of the solution is not critical and can vary widely within the range from approximately neutral to mildly alkaline. Thus, the pH may be greater than or equal to approximately 7.0, preferably from about 8.5 to about 9.5.

The salt is preferably used as part of a buffer solution, the buffering effect created by either the salt itself or by a separate component in the mixture. Conventional buffers can be used, appropriately selected to achieve the desired pH.

For immobilization purposes, the protein A is bound by crosslinking to a solid support, such as the packing material in an affinity chromatography column. Examples of solid supports to which protein A will bind include polyacrylamides, cellulose, and agarose. Agarose is generally preferred.

When the present invention is used to enhance separation in affinity chromatography, it is preferable to equilibrate the column packing by repeated washings with a buffer solution containing a high salt concentration, and also to dilute the sample mixture in the same buffer solution before adding it to the column. The dilution may also vary widely, although dilutions ranging from about 1:1 to about 1:20 are preferred. As the buffer solution passes through the column, non-binding proteins will be carried with the buffer solution which thereby separates them from the bound immunoglobulins. The recovery of the immunoglobulins is then achieved by elution with an acidic buffer, preferably having a pH ranging from about 2.0 to about 5.0, more preferably from about 2.5 to about 4.0.

The nature of the column is not critical and can vary widely, ranging from an open column to a pressurized column. The strong binding inherent in the invention permits an effective separation to be achieved by the use of an open column.

The following examples are for illustrative purposes and are intended neither to limit nor define the invention in any manner.

EXAMPLE 1

A series of binding buffer solutions was prepared for parallel tests, including a standard phosphate buffered saline (0.010M sodium phosphate, 0.15M sodium chloride, pH 8.2). The separation columns were 1 ml open disposable columns each measuring approximately 1 cm in diameter and 2 cm in height, packed with Affi-Gel ®

Protein A (product of Bio-Rad Laboratories, Richmond, Calif.), which is a purified protein A coupled to cross-linked agarose beads through amide bonds.

For each test, a packed column was equilibrated with 5 bed volumes of binding buffer at a flow rate of 0.5 ml/min. A sample of mouse ascites fluid containing an IgG$_1$ monoclonal antibody (9A3) directed against glycophorin A, a human erythrocyte membrane that carries the M and N blood group determinants, was obtained from hybridoma derived from SP2/0 myeloma cells and spleen cells immunized with a mixture of human erythrocytes from homozygous blood groups M and N. The sample was diluted 1:10 with binding buffer and applied to the column in a volume amounting to 10 mg of total protein per ml of Affi-Gel protein A. The column was then washed with ten bed volumes of the binding buffer.

The immunoglobulins were then eluted from the column with three bed volumes of 1.0 M sodium citrate at pH 3, and the eluate was analyzed by ultraviolet absorbance at 280 nm. Percent recovery (equivalent to percent binding on the agarose-protein A) was determined on the basis of an extinction coefficient value of 1.4 absorbent units per mg/ml of immunoglobulin, a value determined by a standard test using excess column packing to bind immunoglobulin, with 100% binding confirmed by gel filtration analysis of the initial eluate.

The results are shown in Table I, from which it is evident that each binding buffer tested demonstrated an improvement over the phosphate-buffered saline (PBS).

TABLE I

BINDING STRENGTH OF 9A3 (IgG$_1$) TO AFFI-GEL ® PROTEIN A USING VARIOUS BINDING BUFFERS

| Binding Buffer | Percent Binding |
| --- | --- |
| 1M (NH$_4$)$_2$SO$_4$ pH 9.0 | 100 |
| 2M Glycine 1M NaCl pH 9.0 | 89 |
| 1M (NH$_4$)$_2$SO$_4$ pH 8.5 | 84 |
| 1M (NH$_4$)$_2$SO$_4$ pH 8.0 | 76 |
| 1M (NH$_4$)$_2$SO$_4$ pH 7.0 | 71 |
| 0.5M (NH$_4$)$_2$SO$_4$ pH 9.0 | 34 |
| PBS pH 8.2 | 16 |

EXAMPLE 2

The test procedure of Example 1 was repeated using, however, a single binding buffer with a series of different monoclonal antibodies of the IgG type. The binding buffer was 1 M (NH$_4$)$_2$SO$_4$ at pH 9.0. The antibodies were all from SP2/0 myeloma cells, and consisted of: the 9A3 of Example 1; 10F7, an IgG$_1$ antibody against glycophorin A; DCMB, an IgG$_1$ of unknown specificity; HOPC-1, an IgG$_{2a}$ of unknown specificity; and T4-1, an IgG$_{2b}$ of unknown specificity. In each case, the percent binding was compared with that achieved by the use of phosphate-buffered saline (PBS) at pH8.2. The results are shown in Table II, demonstrating a clear improvement in every case.

TABLE II

BINDING STRENGTH OF VARIOUS IgG ANTIBODIES TO AFFI-GEL ® PROTEIN A

| | Percent Binding | |
| --- | --- | --- |
| Immunoglobulin | PBS, pH 8.2 | 1M (NH$_4$)$_2$SO$_4$, pH 9.0 |
| IgG$_1$ (9A3) | 16 | 100 |
| IgG$_1$ (10F7) | 15 | 100 |
| IgG$_1$ (DCMB) | 0 | 100 |
| IgG$_{2a}$ (HOPC-1) | 92 | 100 |
| IgG$_{2b}$ (T4-1) | 50 | 100 |

The foregoing description is offered primarily for purposes of illustration. It will be readily apparent to those skilled in the art that numerous modifications and variations of the materials and procedural steps described above may be introduced without departing from the underlying concept and hence the spirit and scope of the invention, which are defined instead by the appended claims.

What is claimed is:

1. A process for binding immunoglobulin G molecules to protein A comprising contacting said molecules with protein A in the presence of an aqueous solution of an inert inorganic salt at a concentration of at least about 0.5 M, such that when the pH of said aqueous solution is less than about 8.0 said concentration is equal to or greater than about 1 M and when said concentration is less than about 1 M said pH is equal to or greater than about 8.0.

2. A process according to claim 1 in which said aqueous solution further contains a buffer at a pH of at least about 7.0.

3. A process according to claim 1 in which said aqueous solution further contains a buffer at a pH of from about 8.5 to about 9.5.

4. A process according to claim 1 in which said salt is selected from the group consisting of ammonium, alkali metal and alkaline earth metal halides and sulfates.

5. A process according to claim 1 in which said protein A is cross-linked with agarose.

6. A process for binding immunoglobulin molecules selected from the group consisting of mouse IgG$_1$, IgG$_{2a}$ and IgG$_{2b}$ to a complex of protein A and agarose, comprising contacting said immunoglobulin molecules with protein A in the presence of an aqueous buffer solution of a salt selected from the group consisting of sodium chloride and ammonium sulfate at a concentration of from about 1.0 M to about 4.0 M and a pH of from about 8.5 to about 9.5.

7. A process for isolating immunoglobulin G molecules from a mixture containing other proteins, comprising:
 (a) passing said mixture through an affinity chromatography column having a solid phase comprising protein A immobilized on a solid support, in the presence of an aqueous solution of an inert inorganic salt, said solution having a concentration of at least about 0.5 M, to selectively bind said immunoglobulin G molecules to said protein A, such that when the pH of said aqueous solution is less than about 8.0 said concentration is equal to or greater than about 1 M and when said concentration is less than about 1 M said pH is equal to or greater than about 8.0; and
 (b) dissociating said immunoglobulin G molecules from said protein A by passing through said column an acid buffer solution.

8. A process according to claim 7 further comprising equilibrating said solid phase prior to step (a) with said aqueous solution.

9. A process according to claim 7 in which said aqueous solution further contains a buffer at a pH of at least about 7.0.

10. A process according to claim 7 in which said aqueous solution further contains a buffer at a pH of from about 8.5 to about 9.5.

11. A process according to claim 7 in which said salt is selected from the group consisting of ammonium, alkali metal and alkaline earth metal halides and sulfates.

12. A process according to claim 7 in which the pH of said acid buffer solution is from about 2.0 to about 5.0.

13. A process according to claim 7 in which the pH of said acid buffer solution is from about 2.5 to about 4.0.

14. A process according to claim 7 in which said solid support is agarose.

15. A process for isolating monoclonal immunoglobulin G molecules from an ascites fluid, said process comprising:

(a) equilibrating an affinity chromatography column having a solid phase comprising protein A cross-linked to an agarose support with an aqueous buffer solution of a salt selected from the group consisting of sodium chloride and ammonium sulfate at a concentration of from about 1.0 M to about 4.0 M and a pH of from about 8.5 to about 9.5;

(b) combining said ascites fluid with a further quantity of said buffer solution to form a solution diluted by from about 1:1 to about 1:20;

(c) applying said diluted solution to said solid phase to selectively bind said immunoglobulin G molecules to said protein A and to pass therethrough the remainder of said ascites fluid;

(d) dissociating said immunoglobulin G molecules from said protein A by passing through said column a buffer solution at a pH of from about 2.5 to about 4.0; and (e) recovering said immunoglobulin G molecules.

16. A process according to claim 1 in which said immunoglobulin G molecules are $IgG_1$ molecules.

* * * * *